(12) United States Patent
Distler et al.

(10) Patent No.: US 7,410,295 B2
(45) Date of Patent: Aug. 12, 2008

(54) GANTRY FOR A COMPUTED TOMOGRAPHY APPARATUS

(75) Inventors: Friedrich Distler, Fürth (DE); Tobias Gnutzmann, Nürnberg (DE); Rita Krug, Fürth (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/514,712

(22) Filed: Aug. 31, 2006

(65) Prior Publication Data

US 2007/0053501 A1 Mar. 8, 2007

(30) Foreign Application Priority Data

Aug. 31, 2005 (DE) .................. 10 2005 041 538

(51) Int. Cl.
*H01J 35/10* (2006.01)
(52) U.S. Cl. .......................................... 378/199; 378/4
(58) Field of Classification Search ................ 378/141, 378/199, 200, 4, 15, 119
See application file for complete search history.

(56) References Cited

U.S. PATENT DOCUMENTS

| | | | |
|---|---|---|---|
| 6,289,073 B1 * | 9/2001 | Sasaki et al. | .................. 378/4 |
| 6,709,156 B1 | 3/2004 | Hell et al. | |
| 6,988,827 B2 | 1/2006 | Mueller | |
| 7,311,439 B2 | 12/2007 | Müller | |

FOREIGN PATENT DOCUMENTS

WO   WO 2005/048843   6/2005

* cited by examiner

*Primary Examiner*—Hoon Song
(74) *Attorney, Agent, or Firm*—Schiff Hardin LLP

(57) ABSTRACT

A gantry for a computed tomography apparatus has a supporting body and a support ring for a rotatable rotary carriage. The supporting body internally exhibits a channel that communicates in terms of flow with the support ring. A cooling ring with a cooling channel is mounted on the radially-inward circumferential side of the support ring. The cross-section of the cooling channel varies in the circumferential direction. The cooling ring exhibits a cooling ring region that has stiffening ribs.

18 Claims, 2 Drawing Sheets

GANTRY FOR A COMPUTED TOMOGRAPHY APPARATUS

BACKGROUND OF THE INVENTION

1. Field of the Invention

The present invention concerns a gantry for a computed tomography apparatus of the type having an outer supporting body and a support ring that supports a rotary carriage, the support ring and the supporting body forming a cooling channel for supply of a coolant to the rotating rotary carriage.

2. Description of the Prior Art

In a computed tomography apparatus, three-dimensional slice images of the inside of a patient are generated by x-ray irradiation. For this purpose, two-dimensional x-ray slice images, from which a three-dimensional slice image is reconstructed, are generated by a scanning unit that normally has an x-ray radiator rotating around the subject and an image acquisition system. The tomography apparatus typically has a stationary part with a support ring that is arranged around a patient acquisition space and a supporting body for the support ring. A rotatable rotary carriage that includes the x-ray radiator and an oppositely-situated x-ray detector is mounted on the support ring. The rotary carriage together with the stationary part is typically called a gantry.

A problem in such a computed tomography apparatus is the dissipation of heat that accumulates in the x-ray radiator and the x-ray detector because 99% of the energy used to generate x-rays is converted into heat. Local air cooling, for example by means of a ventilator, cannot be used or can be used only in a limited manner in a tomography apparatus. The supply and discharge of a gaseous or liquid coolant by means of rigid or flexible coolant lines cannot be realized or can be realized only in a complicated manner, because of the difficulty of configuring such lines so that they do not hinder the required rotation movement capability of the rotary carriage.

Cooling systems conventionally used in such tomography apparatus generally include a number of heat exchangers that are installed inside the support ring. In order to efficiently dissipate heat accumulating at the rotating x-ray radiator from the inside of the rotary carriage, a heat exchanger that rotates with the rotary carriage is conventionally mounted in the immediate proximity of the x-ray radiator. This first heat exchanger emits the heat to the surrounding air. The heated air can be cooled, for example, by a second heat exchanger that dissipates the heat acquired from the air to a cooling system outside of the support ring.

For example, DE 199 45 413 A1 describes a computed tomography apparatus in which the second heat exchanger is mounted stationary relative to the x-ray radiator. The heat absorbed during the operation is dissipated to a cooling system outside of the support ring via coolant lines arranged in a second heat exchanger. It has proven to be disadvantageous that a number of precise mechanical and electrical components are necessary in this arrangement that tend to wear (due to their function) and must be correspondingly serviced. A further disadvantage is in that the gantry must be dimensioned with a relatively large volume due to the size of the heat exchanger required.

An alternative embodiment of a gantry of the type initially described, in which a number of heat exchangers are foregone, is disclosed in PCT Application WO 2005/048843. The computed tomography apparatus according to this publication has a support frame (load-bearing structure) that is fashioned as a hollow section and on which a support ring is attached. The hollow channels that are formed inside the support frame serve for supply and discharge of a coolant.

A problem with this arrangement is an impairment of the stability of the apparatus because the support ring is supported on only one footing formed by two horizontal struts, and a base plate with a series of cavities.

SUMMARY OF THE INVENTION

An object of the present invention is to provide a gantry for a computed tomography apparatus with an efficient cooling system that also exhibits a good stability. A further object is to provide a computed tomography apparatus with such a gantry.

The above object is achieved in accordance with the present invention by a gantry for a computed tomography apparatus having a supporting body and a support ring that supports a rotatable rotary carriage, the support ring having a cooling channel for supply of a coolant to the rotary carriage, with the cooling channel having a cross-section that varies along the circumferential direction thereof.

Cooling of the gantry is achieved that is simple and uncomplicated in terms of design. A coolant is continuously supplied into the cooling channel of the support ring for cooling purposes in the operation of the tomography apparatus. From there the coolant flows out into the space adjacent to the cooling channel where the devices and components to be cooled are located. The cooling channel can extend across the entire circumferential side of the support ring so that the rotating elements of the tomography apparatus can be cooled in a very targeted and effective manner at each point of their orbit.

The varying cross-section of the cooling channel allows free space to be gained adjacent to the cooling channel, and this free space can be used in a suitable manner to increase the rigidity of the support ring and therewith the stability of the entire gantry. A further significant advantage is that the varying cross-section can be adapted to the decreasing quantity of coolant in the cooling channel, such that a uniform flow is ensured and the formation of turbulences (vortices) is avoided. A third advantage of this embodiment is that no heat exchanger must be installed in the support ring. Heat exchangers nevertheless can be additionally provided, complementary to the cooling by the coolant. Such heat exchangers, however, need merely be designed for a comparably smaller additional cooling capacity. Moreover, the parts installed inside the support ring are very simple in terms of design and their production costs are low, so the maintenance costs of the total system are kept low.

In a preferred embodiment the cooling channel has a maximum cross-section and a minimum cross-section, these cross-sections being located approximately diametrically opposite each other. This embodiment can be adapted to the flow direction of the coolant so that the pressure losses in the cooling channel are minimized.

In a further preferred embodiment the cooling ring has a feed opening for the coolant in the region of its maximum cross-section. The coolant flows from the maximum cross-section to the diametrically-opposite minimum cross-section and a portion of the coolant exits for cooling purposes on the path from the cooling channel. The cross-section of the cooling ring that is decreasing in the flow direction is thus effectively adapted to the decreasing coolant quantity by a simple design means.

The transition between the maximum cross-section and the minimum cross-section is furthermore preferably continuous (steady). A particularly good coolant distribution in the cooling channel is thus ensured. The danger of the creation of turbulences and departure from laminar flow is notably reduced by such a continuous transition between the maximum cross-section and the minimum cross-section, and a uniform flow can be set at each point of the cooling channel. Both the pressure loss and the occurring flow noise are reduced in this manner.

A cooling ring with a cross-section that is constant in the circumferential direction, the cross-section accommodating the cooling channel, is arranged in an appropriate manner on the radially-inward circumferential side of the support ring. The cooling channel is thus a part of the cooling ring. This embodiment offers a very simple solution in terms of design for the problem of low rigidity. Free space in the cooling ring that can be used for stiffening ribs is gained with the decreasing cross-section of the cooling channel.

The maximum cross-section of the cooling channel can extend in the radial direction essentially over the entire cooling ring. A particularly large amount of space is thereby available in the region of the maximum cross-section, such that a large quantity of coolant can be supplied and a particularly effective cooling is achieved.

For increased stability of the gantry, stiffening ribs can be attached in the cooling ring region positioned outside of the cooling channel in the circumferential region between the maximum cross-section and the minimum cross-section. At the operating rotating speeds of the rotary carriage of a computed tomography apparatus, oscillation behavior is characterized very strongly by the first eigenmode and the first eigenfrequency associated therewith. The application of the stiffening ribs in the cooling ring region released by the cross-section decrease of the cooling channel increases the first eigenfrequency and thereby increases the rigidity of the gantry.

The cooling ring preferably has a lesser axial extent than that of the support ring. With this embodiment free space is provided next to the cooling ring such that sufficient free space along the entire support ring is guaranteed for the elements to be cooled and that rotate with the rotary carriage.

At least one face of the cooling channel is provided with outlets apertures for supply of the coolant into an axially-adjacent cooling space. This cooling space is bounded by the support ring and the rotary carriage. The coolant escapes from the cooling channel via the outlets and axially acts the rotating elements accommodated in the cooling, space at each point of their orbit. The decreasing coolant quantity in the cooling channel is compensated by the decreasing cross-section of the cooling channel, such that the flow in the cooling channel always remains uniform even after a portion of the coolant escapes in stages from the cooling channel.

In a preferred embodiment the cooling ring is axially positioned centrally within the support ring and is flanked on both sides by cooling spaces. The coolant that flows out of the cooling channel is thereby uniformly distributed around the cooling ring and provides a uniform cooling of the elements on both sides of the cooling ring. Coolant specifically flows through or around the elements to be cooled.

The cooling spaces can contain outlet openings directed radially outwardly for discharge of the coolant into the support ring. The outlet openings extend over the entire outer circumferential side of the cooling spaces and discharge the coolant radially out from the cooling spaces. The coolant ultimately arrives in the supporting body in a fluid path associated with the support ring. This configuration is characterized by a very simple design with a high cooling efficiency.

According to a preferred embodiment the supporting body and the support ring form elements of a coolant circuit (loop). The coolant circulates in the gantry or is held in the supporting body so that no exchange, or only a very slight exchange, with the examination room occurs. Such an embodiment is particularly preferable when a sterile environment is necessary.

In a further embodiment a compressor is provided to compress the coolant. A significant advantage of this embodiment is that such a compressor requires little space and can mounted in the immediate proximity of the supporting body or can be integrated into the supporting body. After the compressor the coolant is supplied directly into the cooling channel in the region of the maximum cross-section. A compact and particularly effective cooling system is thereby achieved.

The thermodynamic effect of the coolant in this embodiment can be further improved by a heat exchanger. The heat exchanger is preferably placed adjacent to the compressor and can be connected to a fluid cooling system such as, for example, a simple water cooling system.

The heat exchanger furthermore is preferably arranged upstream from the compressor in order to cool the coolant before the compression, in particular to below environmental ambient temperature. The upstream heat exchanger likewise can be mounted in the immediate proximity of the supporting body or in the supporting body itself so that the compactness of the cooling system is maintained.

Baffles for directing flow can be appropriately provided in the cooling channel. The desired flow direction of the coolant in the cooling channel is thereby channeled so that a uniform coolant distribution is achieved. The baffles are in particular arranged in the region of the feed opening and conduct the supplied coolant in two semi-circle arcs of the cooling ring. The baffles are appropriately designed and attached at suitable positions in the cooling channel such that an increase of the rigidity is achieved. They thus also serve for additional improvement of the rigidity of the gantry.

Air is advantageously used as the coolant. Cooling with air is particularly economic and effective. Ambient air from the examination room can thereby be used or, alternatively or in combination with the ambient air, the gantry can be connected to one of the pressurized air lines already present anyway in most clinics. Given the use of ambient air, at least one filter is preferably mounted in the gantry, which filters out the dust and other particles in order to prevent the components in the gantry from being contaminated. Furthermore, the cooling air is appropriately dehumidified before entrance into the support ring so that components of the gantry that are at risk of oxidation and the devices located therein are not damaged, and no condensation occurs.

The above object also is achieved in accordance with the present invention by a computed tomography apparatus having a gantry as described above, including all of the aforementioned embodiments.

DESCRIPTION OF THE PREFERRED EMBODIMENTS

Figure 1:
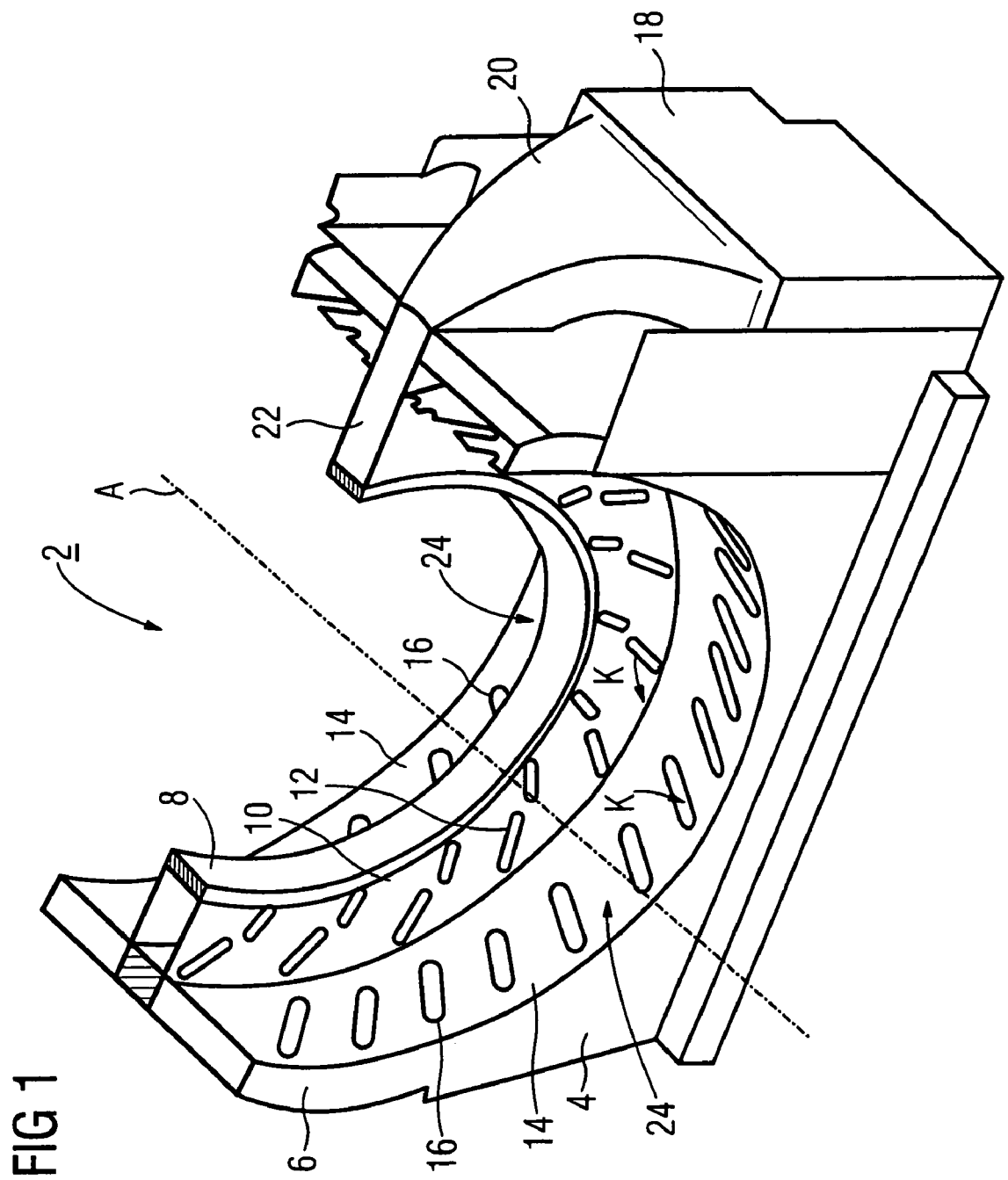
FIG. 1 is a schematic representation of a portion of a gantry of a computed tomography apparatus in accordance with the invention.

FIG. 1 shows a perspective view of a part of a gantry 2. The gantry 2 has a supporting body 4 that has an opening and the lower half of a support ring 6. The supporting body 4 and the support ring 6 are fashioned as one piece and are integrated with one another. The support ring 6 is arranged rotationally symmetrically with respect to an axis A that indicates its axial direction. The support ring 6 has a cooling ring 8 on its radially-inward circumferential side. Both flanks 10 of the cooling ring 8 are provided with outlets 12 that form two rows in the circumferential direction, and the outlets 12 of each row are approximately separated equally from one another. The cooling ring 8 exhibits a smaller axial extent than the support ring 8 and is centrally positioned on the support ring 6 such that two approximately equally large circumferential surfaces 14 are formed on both sides of the cooling ring. Each of the circumferential surfaces 14 exhibits a series of equidistant outlet openings 16. A cooling module 18 is mounted to abut the supporting body 4. The cooling module 18 is connected via a feed line 20 with a cooling channel 22 in the cooling ring 8. The cooling module 18 and the supporting body 4 are connected with one another in terms of flow and can be viewed as a whole, meaning that the cooling module 18 can be considered as a part of the gantry 2.

The gantry 2 has a rotatable rotary carriage that has at least one x-ray radiator and one oppositely-situated x-ray detector. The rotary carriage is mounted around the support ring 6. The rotary carriage thereby covers the spaces over the circumferential surfaces 14 such that two cooling spaces 24 are formed on both sides of the cooling ring 8. The cooling spaces 24 contain the devices and elements (for example the x-ray radiator and the x-ray detector) to be cooled. The annular design of the cooling spaces 24 enables the x-ray radiator and the x-ray detector to rotate as well given rotation of the rotary carriage without hindering its rotation movement capability.

An efficient cooling system for cooling the computed tomography apparatus is achieved by the multiple channels and hollows connected with one another in the gantry 2. A coolant K (in this embodiment air) is fed from the cooling module 18 into the cooling channel 22 of the cooling ring 8 under high pressure via the feed line 20. The coolant K flows axially out from the cooling channel 22 via the outlets 12 into the two cooling spaces 24 in which the elements to be cooled are located. The coolant K flows around the elements heated in the operation of the x-ray radiator and the heat that has permeated into the coolant K is then transported away in a convective manner. The heated coolant K flows radially out from the cooling spaces 24 through the outlet openings 16 and arrives in the hollow inside the supporting body 4. The supporting body 4 is fluidly connected with the cooling module 18, and the coolant K is suctioned by a compressor 26 (see FIG. 2) located in the cooling module 18, compressed and re-supplied to the cooling channel 22 under high pressure. A coolant circuit is formed in the gantry 2 in this manner. In the exemplary embodiment shown in FIGS. 1 and 2 the coolant circuit is closed. A sealed air volume is thus circulated within the gantry 2 and no filters are required for cleaning, for example of environment air. Given an open circuit further openings are provided via which environment air is continuously or discontinuously supplied and also via which a portion of the coolant K in the circuit is discharged.

Figure 2:
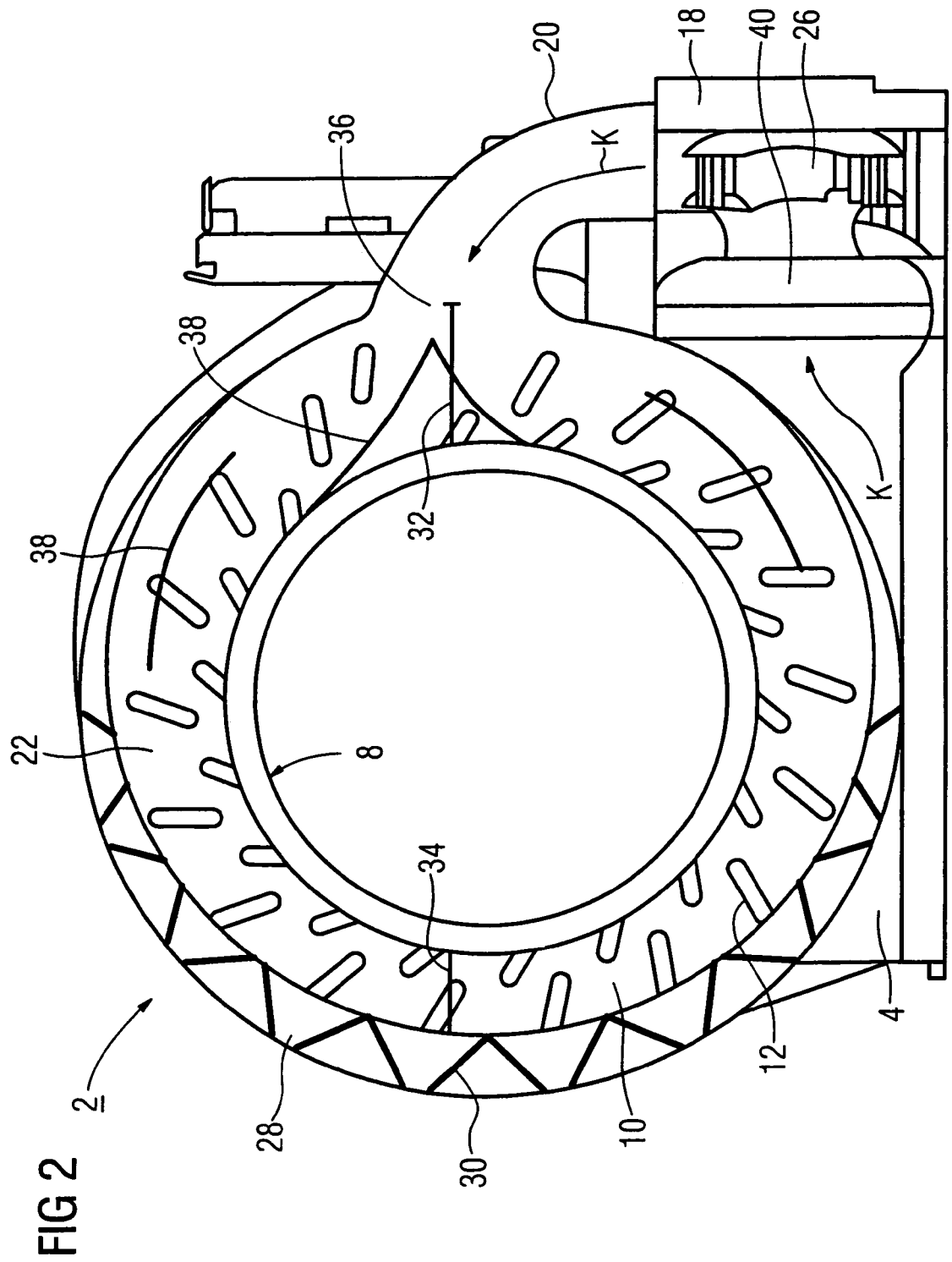
FIG. 2 is a front view of a section in the radial direction through the gantry according to FIG. 1.

The design of the cooling ring 8 is shown in a section through the gantry 2 in the radial direction in FIG. 2. The cooling ring 8 includes the annular cooling channel 22 and a cooling ring region 28 that is provided with stiffening ribs 30. The stiffening ribs 30 fill the cooling ring region 28 like a type of framework structure. The stiffening ribs 30 serve to increase the rigidity and thereby effect an increase of the eigenfrequency of the gantry 2. The cross-section of the cooling channel 22 varies in the circumferential direction and exhibits a maximum cross-section 32 and an approximately diametrically-opposed minimal cross-section 34. The maximum cross-section 32 extends in the radial direction over the entire cooling ring 8 and is positioned in the region in which the feed line empties into the cooling channel 22. In this region the cooling channel exhibits a feed opening 36 for the coolant air K. The cross-section of the cooling channel 22 steadily decreases in the direction of the minimum cross-section 34 such that the cooling ring region 28 is created in the circumferential region outside of the cooling channel 22. The flank 10 of the cooling channel 22 or of the cooling ring 8 is provided with a number of outlets 12 that are arranged circularly over the entire circumference of the flank 10. Moreover, baffles 38 are arranged inside the cooling channel 22 that enable a better distribution of the coolant air K in that they support its flow direction. The baffles 38 can also be fashioned from other materials in addition to metal.

Upon inflow of coolant K into the cooling channel 22 in the region of the maximum cross-section 32, the flow splits in two directions (abetted by the baffles 38) and flows over the two semi-circular arcs of the cooling ring 8 in the direction toward the minimum cross-section 34. On its way a portion of the coolant air K continuously flows out of the coolant channel 22 through the outlets 12 and radially arrives in the adjacent cooling spaces 24. Via the steadily-decreasing cross-section the flow cross-section of the cooling channel 22 is adapted to the quantity of coolant K decreasing from the feed opening 36 toward the region with the minimum cross-section 34, such that a uniform flow is ensured. The arrangement of a uniform flow reduces the danger of turbulences and detachments as well as the arising flow noises.

After flowing out from the cooling spaces 24, the coolant air K that has been heated arrives in the channel of the supporting body 4. The supporting body 4 is connected with the cooling module 18 and the compressor 26 located in the cooling module 18 compresses the coolant air K in the supporting body 4. A heat exchanger 40 that provides for a cooling of the coolant air K (in particular to below environment temperature) before the compression is located upstream from the compressor 26. After the compression the coolant air K is re-supplied to the cooling channel 22 under high pressure via the feed line 20 and the supply opening 36. Upon expanding in the cooling channel 22, the temperature of the coolant air K decreases. Due to the overpressure and the high flow speeds of the coolant air K after the compressor 26, suitable precautions are taken in order to prevent leakages and to ensure a safe and efficient cooling of the computed tomography apparatus.

Although modifications and changes may be suggested by those skilled in the art, it is the intention of the inventors to embody within the patent warranted hereon all changes and modifications as reasonably and properly come within the scope of their contribution to the art.

We claim as our invention:

1. A gantry for a computed tomography apparatus, comprising:

a supporting body;

a support ring mounted in said supporting body, said support ring supporting a rotary carriage that is rotatable in said support ring in a rotation direction, and said support ring comprising a cooling channel for supply of a coolant to the rotary carriage, said cooling channel continuously proceeding around said support ring in a circumferential direction corresponding to said rotation direction; and said cooling channel having a cross-section that varies along said circumferential direction.

2. A gantry as claimed in claim 1 wherein said cooling channel has a maximum cross-section and a minimum cross-section, said maximum cross-section and said minimum cross-section being approximately opposite each other along said circumferential direction.

3. A gantry as claimed in claim 2 wherein said cooling channel has a feed opening for said coolant disposed in proximity to said maximum cross-section.

4. A gantry as claimed in claim 2 wherein said channel has a continuous transition between said maximum cross-section and said minimum cross-section.

5. A gantry as claimed in claim 1 comprising a cooling ring having a constant cross-section along said circumferential direction, said cooling ring being disposed inside said support ring, and said support ring having a radially-inward circumferential side, facing said cooling ring, with said cooling ring and said support ring forming said cooling channel therebetween.

6. A gantry as claimed in claim 1 wherein said cooling channel has a maximum cross-section and a minimum cross-section, said maximum cross-section extending radially around substantially an entirety of said cooling ring.

7. A gantry as claimed in claim 6 wherein said cooling ring has a cooling ring region beyond said cooling channel in said circumferential direction, between said maximum cross-section and said minimum cross-section of said cooling channel, said cooling ring region comprising stiffening ribs therein.

8. A gantry as claimed in claim 5 wherein each of said cooling ring and said support ring have an axial extent perpendicular to said circumferential direction, with the axial extent of said cooling ring being smaller than the axial extent of said support ring.

9. A gantry as claimed in claim 1 wherein said supporting body comprises a cooling space that is axially adjacent to said cooling channel, and wherein said cooling channel has at least one face comprising a plurality of outlets that allow coolant to flow from said cooling channel into said cooling space.

10. A gantry as claimed in claim 9 comprising a cooling ring having a constant cross-section along said circumferential direction, said cooling ring being disposed inside said support ring, and said support ring having a radially-inward circumferential side, facing said cooling ring, with said cooling ring and said support ring forming said cooling channel therebetween, said cooling ring being disposed axially centrally inside said support ring, and said supporting body having two cooling spaces respectively disposed at opposite sides of said cooling ring.

11. A gantry as claimed in claim 10 wherein each of said cooling spaces comprises radially outwardly directed openings allowing discharge of said coolant into said support ring.

12. A gantry as claimed in claim 1 wherein said supporting body and said support ring comprise components of a closed loop for said coolant.

13. A gantry as claimed in claim 12 comprising a compressor in fluid communication with said closed loop, said compressor compressing said coolant in said closed loop.

14. A gantry as claimed in claim 13 comprising a heat exchanger in thermal communication with said coolant.

15. A gantry as claimed in claim 14 wherein said heat exchanger is in thermal communication with said coolant in said closed loop, and is disposed upstream, in terms of flow of said coolant, from said compressor.

16. A gantry as claimed in claim 1 comprising baffles disposed in said cooling channel to direct flow of said coolant in said cooling channel.

17. A gantry as claimed in claim 1 wherein said channel contains air as said coolant.

18. A computed tomography apparatus comprising:
a rotary carriage carrying x-ray imaging equipment; and
a gantry comprising a supporting body, a support ring mounted in said supporting body, said support ring supporting said rotary carriage for rotation of the rotary carriage in a rotation direction, and said support ring comprising a cooling channel for supply of a coolant to the rotary carriage, said cooling channel proceeding continuously around said support ring in a circumferential direction corresponding to said rotation direction, and said cooling channel having a cross-section that varies along said circumferential direction.

* * * * *